United States Patent
Qiu et al.

(10) Patent No.: US 10,017,407 B2
(45) Date of Patent: Jul. 10, 2018

(54) PROCESS FOR MANUFACTURING COLLAGEN AND TRACE ELEMENTS FROM SEA WATER

(71) Applicant: Seawagen Co., Ltd., Bangkok (TH)

(72) Inventors: Yongsheng Qiu, Bangkok (TH); Hsin-Ken Wang, Phingjeon (TH)

(73) Assignee: Seawagen Co., Ltd., Bangkok (TH)

( * ) Notice: Subject to any disclaimer, the term of this patent is extended or adjusted under 35 U.S.C. 154(b) by 0 days.

(21) Appl. No.: 14/536,183

(22) Filed: Nov. 7, 2014

(65) Prior Publication Data

US 2015/0065430 A1    Mar. 5, 2015

Related U.S. Application Data

(63) Continuation-in-part of application No. 13/638,071, filed as application No. PCT/TH2010/000026 on Jul. 30, 2010, now abandoned.

(30) Foreign Application Priority Data

Jan. 11, 2010   (TH) ................................ 1001000037

(51) Int. Cl.
| | | |
|---|---|---|
| *C02F 9/00* | (2006.01) | |
| *A61K 38/39* | (2006.01) | |
| *A61K 35/08* | (2015.01) | |
| *C02F 101/20* | (2006.01) | |
| *C02F 103/08* | (2006.01) | |
| *C02F 1/00* | (2006.01) | |
| *C02F 1/48* | (2006.01) | |
| *C02F 1/74* | (2006.01) | |
| *C02F 103/02* | (2006.01) | |

(52) U.S. Cl.
CPC ............... *C02F 9/00* (2013.01); *A61K 35/08* (2013.01); *A61K 38/39* (2013.01); *C02F 1/001* (2013.01); *C02F 1/48* (2013.01); *C02F 1/74* (2013.01); *C02F 2101/20* (2013.01); *C02F 2103/026* (2013.01); *C02F 2103/08* (2013.01); *C02F 2301/066* (2013.01); *C02F 2303/02* (2013.01)

(58) Field of Classification Search
None
See application file for complete search history.

(56) References Cited

U.S. PATENT DOCUMENTS

| 5,595,666 A | * | 1/1997 | Kochen ................... B01J 41/04 210/679 |
| 2007/0087039 A1 | * | 4/2007 | Gu ......................... C07K 14/78 424/442 |
| 2009/0045116 A1 | | 2/2009 | Escribano |

FOREIGN PATENT DOCUMENTS

CN            1749296 A        3/2006

OTHER PUBLICATIONS

Primer for Municipal Wastewater Treatment Systems, United States Environmental Protection Agency (2004) 1-30.*
Gross, J. Biol. Chem. (1958) 233, 355-360.*
Seawagen website, http://www.tracelement.com/ (2009).*
Cheryl Podsiki, AIC-PA, Health & Safety Committee, Nov. 2008, available at http://www.conservation-us.org/docs/default-source/resource-guides/chart-of-heavy-metals-their-salts-and-other-compounds.pdf.*
Seawagen website (http://www.tracelement.com/ (2009)).*
Primer for Municipal Wastewater Treatment Systems ("EPA primer") (United States Environmental Protection Agency (2004) 1-30).*
Gross et al., (J. Biol. Chem. (1958) 233, 355-360).*
Aldrich catalog (Sigma-Aldrich Co. (2005-2006) pp. E184 and E223).*
Sigma-Aldrich catalog available at http://www.sigmaaldrich.com/catalog/product/aldrich/z232459?lang=en&region=US&gclid=CJue-57S7dQCFZSNswodiGAKdQ.*
Greenberg, Anal. Chem. 1983, 55, 1160-1165 (Year: 1983).*
International Search Report issued in International Application No. PCT/TH2010/000026 dated Dec. 23, 2010

* cited by examiner

*Primary Examiner* — Satyanarayana R Gudibande
(74) *Attorney, Agent, or Firm* — Michael T. Abramson; Holland & Knight LLP

(57) ABSTRACT

The process for manufacturing collagen and trace elements from sea water consists of various steps which are raw material preparation, resting of raw material, preliminary filtration to remove heavy metals, deodorize and purity remaining impurities, spraying of water, separation of heavy metals, collagen and trace elements from water and separation of collagen and trace elements. The process according to this invention, apart from sea water, can be applied to other type of salt water by adjusting the salinity and density of the water to an optimal value. The process according to this invention yields clean and purified collagen which is easily absorbed by human body and contains numerous types of trace elements.

11 Claims, No Drawings

PROCESS FOR MANUFACTURING COLLAGEN AND TRACE ELEMENTS FROM SEA WATER

FIELD OF THE INVENTION

Food sciences and technology related to process for manufacturing collagen and trace elements from sea water

BACKGROUND OF THE INVENTION

Collagen is the composition of tissues between cells in the human body. Currently, collagen has been used in cosmetic, nutraceutical, pharmaceutical and medical products. The benefits of collagen are, for instance, wound healing, adjusting equilibrium of epidermis, retaining moisture of skin and improving flexibility of subcutaneous tissues.

From the scientific discovery, collagen (33% in form of egg white) is in human body's structure. After 25 years, collagen within the body decreases at the rate of approximately 1.5%.

Trace elements or micro elements are present in the human body less than 0.01% of body weight. At present, 80 trace elements in human body have been found. The significance of trace elements to human body includes;
1. Protect the normal function of human body
2. Control circulation in cell and systems
3. Improve immune.
4. Enhance cell potentials In general, the processes of manufacturing collagen include chemical separation and separation by fermentation and raw materials are derived from terrestrial and aquatic animals as well as selected plants. In case of terrestrial animals i.e. cow, pig, goat and chicken, the starting materials are skin, bone and tendons. In case of aquatic animals i.e. fish and shrimp, the starting materials are shell, skin and bone whereas, in case of plant, the starting material is bark.

The said general processes of manufacturing collagen yield acidic collagen with only a few types of trace elements which cannot be adjusted for application in human completely.

SUMMARY OF THE INVENTION

This invention is related to the process for manufacturing collagen and trace elements from sea water or salt water. The process includes the steps of raw material preparation; resting of raw material; preliminary filtration to remove heavy metals, deodorize and purify remaining impurities; spraying of water, heavy metals, collagen and trace elements separation from water and separation of collagen and trace elements.

The aim of this invention is to provide the process for manufacturing collagen and trace elements from sea water or salt water by using sea water or salt water as raw material. Sea water comprises marine organism which is a convenient source of collagen.

Furthermore, deep sea water has an abundance of trace elements indispensable for the human body which include magnesium, calcium, potassium, iron, iodine, zinc, phosphorus, copper, chromium, etc. Since the deep sea water is unreachable by sunlight, the photosynthesis, which requires inorganic salts contributing to growth and reproduction of plant plankton and algae, barely occurs. Therefore, trace elements and minerals in deep sea water have been preserved and accumulated over the years. This process, therefore, yields the purified collagen which is easy to be absorbed by human body and contains numerous types of trace elements.

Collagen extracted from sea water has the smallest size of molecular weight (3000) when compared to collagens derived from animals (terrestrial and aquatic).

Collagen containing high amount of trace elements is essential for human body. The coordinating angle of human body is close to the coordinating angle of sea water which is between 165-180° whereas the coordinating angle of freshwater is 130°. This makes the collagen with high amount of trace elements easy to be absorbed.

Therefore the extraction of collagen and trace elements from sea water is not only important for the pharmaceutical and cosmetic applications but also for the human well-being and disease prevention.

The other objectives of this invention can be understood by the person skilled in the art according to the detail description of this invention.

DETAILED DESCRIPTION OF THE INVENTION

The following details describe the process for manufacturing collagen and trace elements from sea water in order to further explain the details of this invention.

The process for manufacturing collagen and trace elements from sea water according to this invention includes the steps;

(1) Raw Material Preparation:

In this step, the sea water is transferred to the container with air circulation in order to ventilate the air, deodorize, purify impurities and remove heavy metals from the said sea water.

Raw materials according to this invention, besides the said sea water, another type of salt water may also be used as the raw materials, for example, saline water (prepared from salts). In order to optimize the process, when salt is used to prepare saline for the process according to this invention, the salinity and density should be adjusted to the optimal values.

Moreover, the containers can be selected from but not limited to non-metal bucket, well or any other containers.

(2) Resting of Raw Material

In this step, the raw material is rested for a certain period of time according to its type.

Seawater is rested for 1-2 days

Salt water is rested for 2-3 days (3) Preliminary Filtration to Remove Heavy Metals, Deodorize and Purify Remaining Impurities This step involves re-filtering the sea water or salt water resulting in multiple transferring of raw material in order to deodorize, purify remaining impurities and remove heavy metals i.e. mercury and lead from the water and to aerate and foam in order to deodorize and purify the remaining impurities. This step yields clean and odorless water.

The process in this step is performed by passing the sea water or salt water into the filtering machine repeatedly.

(4) Spraying of Water

The water obtained from (3) will be sprayed within the tube under the controlled temperature and flow rate and re-filtered with the filtering machine before storing in a resting container.

The said resting container includes a resting bucket or any other resting containers.

(5) Separation of Heavy Metals, Collagen and Trace Elements from Water

The water obtained from (4) is passed through the separation machine by circulating water within the separation machine several times in order to remove heavy metals. The heavy metals are then collected whereas collagen and trace elements are still binding and suspending in water.

The separation machine is based on the magnetic field and able to separate heavy metals, collagen and trace elements. Large-grained and high-density heavy metals are precipitated while collagen and trace elements are suspended in the water. Suspended collagen and trace elements make the appearance of water milky and the salinity reduced.

(6) Separation of Collagen and Trace Elements

In this step, the water with reduced salinity and milky appearance obtained from (5) will be precipitated in order to separate collagen and trace elements or the said water can be filtered with fine filter cloth in order to remove collagen and trace elements. The separation can be done with any other methods. The collagen and trace elements obtained from this step is grayish-white gel-like liquid.

To obtain a better result, the step of raw material preparation should be conducted under controlled pressure and light of the sea water so that it optimally helps to generate collagen and trace elements in a sufficiently large amount.

In addition, in order to obtain a better result, the step of preliminary filtration to remove heavy metals, remaining impurities and deodorize should be conducted by increasing pressure and oxygen in order to reduce the size of the elements molecules, making it easier for the microbes to absorb these elements and encouraging microbes to grow faster and live longer.

The process for manufacturing collagen and trace elements from sea water according to the invention yields the purified collagen which is easily absorbed by human body and contains many types of trace elements that are essential for human body. The table below shows the amount of trace elements in a sample product obtained by the process according to the present invention.

TABLE

Trace element analysis of sample product

| Trace element | Amount (mg/kg) |
|---|---|
| Cu | 2.43 |
| Cr | 10.4 |
| Ni | 2.89 |
| Na | 3480 |
| Fe | 41.4 |
| Zn | 28.2 |
| Mn | 5.63 |
| K | 114 |
| Mg | 7390 |
| Ca | 310 |
| Ba | 0.21 |
| Li | 4.51 |
| Ga | 1.69 |
| Sr | 7.36 |
| Ti | 2.51 |
| Si | 8.08 |
| As | 0.0672 |
| Hg | 0.011 |

The process for manufacturing collagen and trace elements from sea water according to this invention may be modified and altered within the scope of the invention.

The invention claimed is:

1. A process for manufacturing collagen and trace elements comprising:
    (a) preparing raw material comprising:
        (i) storing sea water in a container under controlled pressure and lighting;
        (ii) providing preliminary air ventilation and deodorization;
        (iii) removing impurities by filtering the sea water, wherein the filtering removes heavy metals;
    (b) deodorizing the sea water comprising:
        (i) increasing the pressure and oxygen concentration to foam the sea water;
    (c) spraying the sea water into a tube under a controlled temperature and flow rate;
    (d) re-filtering the sea water; and
    (e) separating, in the presence of a magnetic field, the remaining heavy metals from the collagen and the trace elements from the sea water.

2. The process for manufacturing collagen and trace elements according to claim 1 wherein the raw material is rested following the raw material preparation.

3. The process for manufacturing collagen and trace elements according to claim 1 wherein salinity and density of the raw material are adjustable.

4. The process for manufacturing collagen and trace elements according to claim 2 wherein the container for resting of the raw material is a bucket.

5. The process for manufacturing collagen and trace elements according to claim 2 wherein the resting of the raw material is performed by resting the sea water in the container for 1-2 days.

6. The process for manufacturing collagen and trace elements according to claim 1 wherein the filtering of the sea water in order to remove heavy metals is performed by passing the sea water into a filtering machine a plurality of times.

7. The process for manufacturing collagen and trace elements according to claim 1 wherein a separation machine is based on the magnetic field and is able to separate the heavy metals from the collagen and the trace elements.

8. The process for manufacturing collagen and trace elements according to claim 1 wherein after separating the remaining heavy metals from the collagen and trace elements, the collagen and the trace elements are suspended in the sea water.

9. The process for manufacturing collagen and trace elements according to claim 8 wherein after separating the remaining heavy metals from the collagen and trace elements, salinity of the sea water is reduced and the appearance of the sea water is milky.

10. The process for manufacturing collagen and trace elements according to claim 9 wherein the separation of the collagen and the trace elements is performed by precipitation from the sea water.

11. The process for manufacturing collagen and trace elements according to claim 10 wherein the separation of the collagen and the trace elements is performed by filtration of the sea water using a fine filter cloth.

* * * * *